(12) United States Patent
Beckman et al.

(10) Patent No.: US 7,749,161 B2
(45) Date of Patent: Jul. 6, 2010

(54) HAND ASSISTED LAPAROSCOPIC DEVICE

(75) Inventors: Andrew T. Beckman, Cincinnati, OH (US); Carrie I. Fihe, Cincinnati, OH (US); William J. White, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 810 days.

(21) Appl. No.: 11/607,118

(22) Filed: Dec. 1, 2006

(65) Prior Publication Data

US 2008/0132765 A1 Jun. 5, 2008

(51) Int. Cl.
*A61B 1/00* (2006.01)
(52) U.S. Cl. ....................................... 600/208
(58) Field of Classification Search ................ 600/201, 600/203, 204, 206, 208, 210; 74/575, 578, 74/527, 531; 220/86.2; 215/216, 230
See application file for complete search history.

(56) References Cited

U.S. PATENT DOCUMENTS

| 5,046,740 A | 9/1991 | D'Eath |
| 5,183,409 A | 2/1993 | Clever et al. |
| 5,211,370 A | 5/1993 | Powers |
| 5,366,478 A | 11/1994 | Brinkerhoff et al. |
| 5,437,683 A | 8/1995 | Meumann et al. |
| 5,480,410 A | 1/1996 | Cuschieri et al. |
| 5,514,133 A | 5/1996 | Golub et al. |
| 5,522,791 A | 6/1996 | Leyva |
| 5,524,644 A | 6/1996 | Crook |
| 5,526,536 A | 6/1996 | Cartmill |
| 5,545,179 A | 8/1996 | Williamson, IV |
| 5,613,938 A | 3/1997 | Kaiser et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,653,717 A | 8/1997 | Ko et al. |
| 5,672,168 A | 9/1997 | de la Torre et al. |
| 5,741,298 A | 4/1998 | MacLeod |
| 5,803,921 A | 9/1998 | Bonadio |
| 5,810,721 A | 9/1998 | Mueller et al. |
| 5,853,395 A | 12/1998 | Crook et al. |
| 5,871,474 A | 2/1999 | Hermann et al. |
| 5,899,208 A | 5/1999 | Bonadio |
| 5,906,577 A | 5/1999 | Beane et al. |
| 5,925,064 A | 7/1999 | Meyers et al. |

(Continued)

FOREIGN PATENT DOCUMENTS

EP 0887047 12/1998

(Continued)

*Primary Examiner*—Todd E Manahan
*Assistant Examiner*—Christopher Schubert
(74) *Attorney, Agent, or Firm*—Welsh & Flaxman LLC

(57) ABSTRACT

A seal assembly for permitting hand assisted laparoscopic procedures includes a seal cap having an iris seal positioned within a housing. The housing includes a lower seal ring having a track which supports an upper seal ring for relative rotational motion, wherein the iris seal is supported between the upper seal ring and the lower seal ring for rotation between an open orientation and a closed orientation. The seal assembly also includes a retractor extending from the seal cap.

15 Claims, 8 Drawing Sheets

U.S. PATENT DOCUMENTS

| | | |
|---|---|---|
| 5,947,922 A | 9/1999 | MacLeod |
| 5,957,913 A | 9/1999 | de la Torre et al. |
| 5,964,781 A | 10/1999 | Mollenauer et al. |
| 6,024,736 A | 2/2000 | de la Torre et al. |
| 6,033,426 A | 3/2000 | Kaji |
| 6,033,428 A | 3/2000 | Sardella |
| 6,048,309 A | 4/2000 | Flom et al. |
| 6,110,154 A | 8/2000 | Shimomura et al. |
| 6,142,935 A | 11/2000 | Flom et al. |
| 6,142,936 A | 11/2000 | Beane et al. |
| 6,149,642 A | 11/2000 | Gerhart et al. |
| 6,159,200 A | 12/2000 | Verdura et al. |
| 6,165,184 A | 12/2000 | Verdura et al. |
| 6,228,022 B1 | 5/2001 | Friesem et al. |
| 6,254,533 B1 | 7/2001 | Fadem et al. |
| 6,254,534 B1 | 7/2001 | Butler et al. |
| 6,315,770 B1 | 11/2001 | de la Torre et al. |
| 6,319,246 B1 | 11/2001 | de la Torre et al. |
| 6,382,211 B1 | 5/2002 | Crook |
| 6,440,063 B1 | 8/2002 | Beane et al. |
| 6,450,983 B1 | 9/2002 | Rambo |
| 6,485,467 B1 | 11/2002 | Crook et al. |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,613,952 B2 | 9/2003 | Rambo |
| 6,623,426 B2 | 9/2003 | Bonadio et al. |
| 6,676,706 B1 | 1/2004 | Mears et al. |
| 6,723,044 B2 | 4/2004 | Pulford et al. |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,817 B2 | 3/2005 | Middleton |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,945,935 B1 | 9/2005 | Sasse et al. |
| 6,958,037 B2 | 10/2005 | Ewers et al. |
| 7,008,377 B2 | 3/2006 | Beane et al. |
| 7,052,411 B2 | 5/2006 | Solheim et al. |
| 7,059,971 B1 | 6/2006 | Schmitt |
| 7,300,399 B2 | 11/2007 | Bonadio et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0038077 A1 | 3/2002 | de la Torre et al. |
| 2002/0068923 A1 | 6/2002 | Caldwell et al. |
| 2002/0072762 A1 | 6/2002 | Bonadio et al. |
| 2002/0162559 A1 | 11/2002 | Crook |
| 2002/0183594 A1 | 12/2002 | Beane et al. |
| 2003/0062051 A1 | 4/2003 | Rambo |
| 2003/0078478 A1 | 4/2003 | Bonadio et al. |
| 2003/0176771 A1 | 9/2003 | Pulford et al. |
| 2003/0187376 A1 | 10/2003 | Rambo |
| 2003/0192553 A1 | 10/2003 | Rambo |
| 2004/0012772 A1 | 1/2004 | Ahn et al. |
| 2004/0015185 A1 | 1/2004 | Ewers et al. |
| 2004/0049099 A1 | 3/2004 | Ewers et al. |
| 2004/0049100 A1 | 3/2004 | Butler et al. |
| 2004/0073090 A1 | 4/2004 | Butler et al. |
| 2004/0092795 A1 | 5/2004 | Bonadio et al. |
| 2004/0092796 A1 | 5/2004 | Butler et al. |
| 2004/0097793 A1 | 5/2004 | Butler et al. |
| 2004/0106942 A1 | 6/2004 | Taylor et al. |
| 2004/0154624 A1 | 8/2004 | Bonadio et al. |
| 2004/0173218 A1 | 9/2004 | Yamada et al. |
| 2004/0242344 A1 | 12/2004 | Williams et al. |
| 2004/0249248 A1 | 12/2004 | Bonadio et al. |
| 2004/0260153 A1 | 12/2004 | Pulford et al. |
| 2004/0267096 A1 | 12/2004 | Caldwell et al. |
| 2005/0020884 A1 | 1/2005 | Hart et al. |
| 2005/0022779 A1 | 2/2005 | Hattori et al. |
| 2005/0043592 A1 | 2/2005 | Boyd et al. |
| 2005/0113821 A1 | 5/2005 | Pendekanti et al. |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0222582 A1* | 10/2005 | Wenchell .................. 606/108 |
| 2005/0240082 A1 | 10/2005 | Bonadio et al. |
| 2005/0241647 A1 | 11/2005 | Nguyen et al. |
| 2005/0267419 A1 | 12/2005 | Smith |
| 2006/0014590 A1 | 1/2006 | Tao |
| 2006/0030755 A1 | 2/2006 | Ewers et al. |
| 2006/0047284 A1 | 3/2006 | Gresham |
| 2006/0047293 A1 | 3/2006 | Haberland et al. |
| 2006/0084842 A1 | 4/2006 | Hart et al. |
| 2006/0149306 A1 | 7/2006 | Hart et al. |

FOREIGN PATENT DOCUMENTS

| | | |
|---|---|---|
| EP | 0887048 | 12/1998 |
| EP | 0888755 | 1/1999 |
| EP | 1125552 | 8/2001 |
| EP | 1407715 | 4/2004 |
| EP | 1415610 | 5/2004 |
| EP | 1495728 | 1/2005 |
| WO | WO95/07056 | 3/1995 |
| WO | WO95/22289 | 8/1995 |
| WO | WO96/20749 | 7/1996 |
| WO | WO99/25268 | 5/1999 |
| WO | WO00/32116 | 6/2000 |
| WO | WO00/32117 | 6/2000 |
| WO | WO00/32120 | 6/2000 |
| WO | WO00/54675 | 9/2000 |
| WO | WO00/54676 | 9/2000 |
| WO | WO00/54677 | 9/2000 |
| WO | WO01/08563 | 2/2001 |
| WO | WO01/08581 | 2/2001 |
| WO | WO01/26558 | 4/2001 |
| WO | WO02/34108 | 5/2002 |
| WO | WO03/086202 | 10/2003 |
| WO | WO03/103548 | 12/2003 |
| WO | WO2004/026153 | 4/2004 |
| WO | WO2004/030547 | 4/2004 |
| WO | WO2004/032753 | 4/2004 |
| WO | WO2004/049902 | 6/2004 |
| WO | WO2004/054456 | 7/2004 |
| WO | WO2004/075730 | 9/2004 |
| WO | WO2004/075741 | 9/2004 |
| WO | WO2004/093699 | 11/2004 |
| WO | WO2004/096012 | 11/2004 |
| WO | WO2005/034766 | 4/2005 |
| WO | WO2005/089661 | 9/2005 |
| WO | WO2005/097019 | 10/2005 |
| WO | WO2005/097234 | 10/2005 |
| WO | WO2005/102185 | 11/2005 |

* cited by examiner

FIG. 6
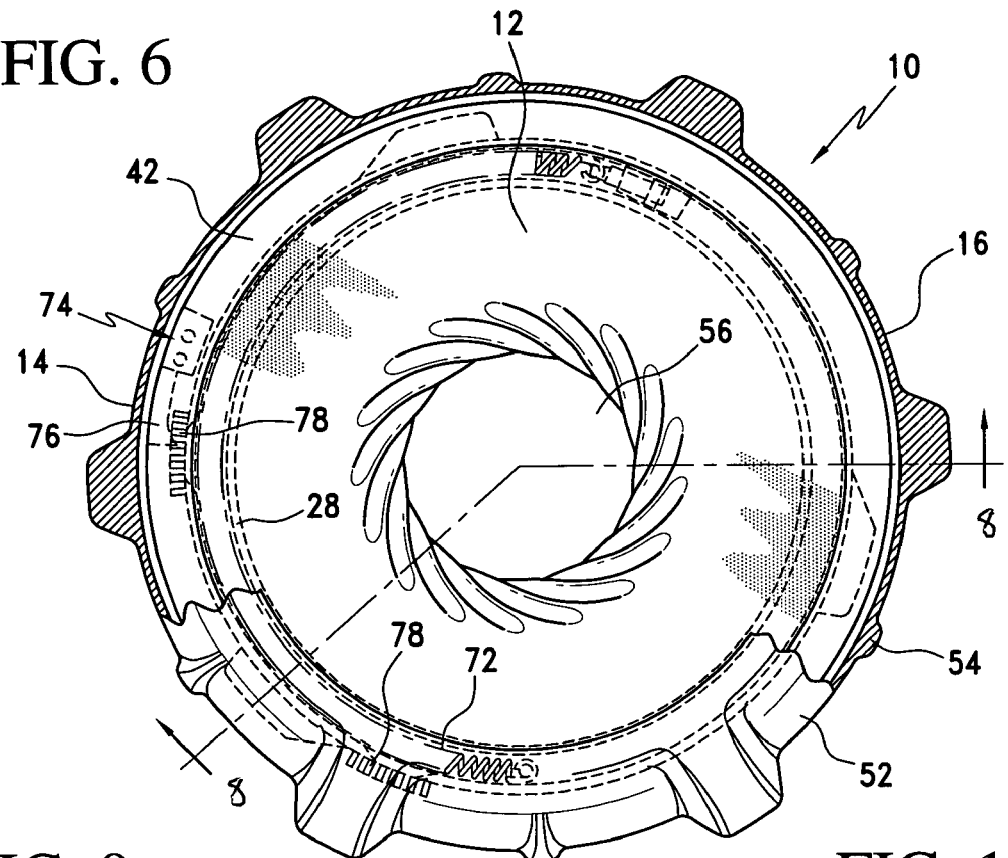
FIG. 9
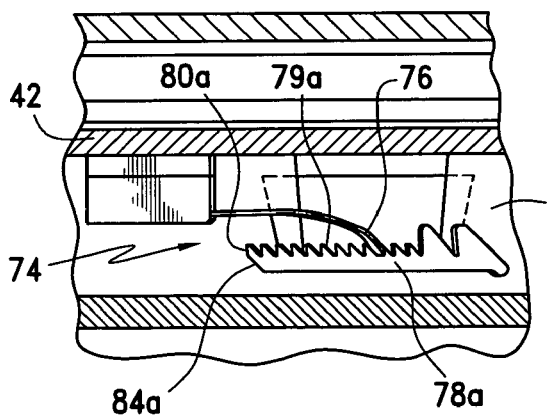
FIG. 10
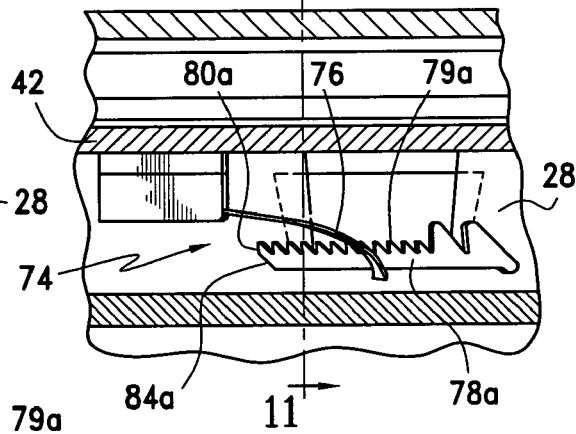
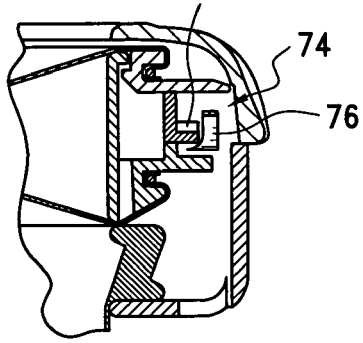
FIG. 11

HAND ASSISTED LAPAROSCOPIC DEVICE

BACKGROUND OF THE INVENTION

1. Field of the Invention

The invention relates to laparoscopic devices. In particular, the invention relates to a laparoscopic seal assembly permitting the use of hands in assisting during laparoscopic procedures.

2. Description of the Prior Art

During laparoscopic procedures, it is often desirable for the surgeon to place his or her hand within the patient in a manner manipulating the instruments positioned within the patient. When this occurs, it is desirable to separate the external environment from the internal portion of the patient. For example, when hand assisted laparoscopic procedures are performed within the abdominal cavity, it is desirable to perform hand exchanges with minimal loss of abdominal insufflation. As such, a need exists for skin mountable seals permitting hand assisted laparoscopic procedures without fear that the abdominal pressure will be compromised. The present invention provides such an apparatus.

SUMMARY OF THE INVENTION

It is, therefore, an object of the present invention to provide a seal assembly for permitting hand assisted laparoscopic procedures. The seal assembly includes a seal cap having an iris seal positioned within a housing. The housing includes a lower seal ring having a track which supports an upper seal ring for relative rotational motion, wherein the iris seal is supported between the upper seal ring and the lower seal ring for rotation between an open orientation and a closed orientation. The seal assembly also attaches to a retractor extending from the seal cap.

It is also an object of the present invention to provide a seal assembly wherein the housing further connects to an attachment ring detachably secured to the lower seal ring for permitting selective attachment of the retractor by positioning it between the attachment ring and the lower seal ring.

It is also another object of the present invention to provide a seal assembly wherein the lower seal ring includes at least one outwardly extending flange shaped and dimensioned for seating within at least one inwardly facing recess formed along the attachment ring.

It is also a further object of the present invention to provide a seal assembly where an upper end of the iris seal is connected to the upper seal ring and a lower end of the iris seal is connected to the lower seal ring.

It is another object of the present invention to provide a seal assembly including an ergonomic cover member secured to the upper seal ring, wherein the ergonomic cover member includes a contoured outer surface providing for improved handling and twisting of the upper seal ring for opening and closing the iris seal.

It is a further object of the present invention to provide a seal assembly wherein the iris seal is constructed in a folded configuration spanning the upper seal ring and the lower seal ring.

It is still a further object of the present invention to provide a seal assembly wherein the iris seal is composed of a rubber like material.

It is yet another object of the present invention to provide a seal assembly including a contoured ring secured to the upper seal ring, the contoured ring including an inner circumference formed with a series of recesses shaped and dimensioned for receiving fingers of a user.

It is also an object of the present invention to provide a seal assembly including a spring biasing the upper seal ring relative to the lower seal ring.

It is another object of the present invention to provide a seal assembly including a ratchet mechanism controlling motion of the upper seal ring relative to the lower seal ring.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 4, 5 and 6 are partial sectional top views showing actuation of the present hand assisted laparoscopic seal assembly respectively between a closed position, a partially opened orientation for hand insertion and a fully opened orientation for viewing and insertion of larger instruments or specimen extraction.

FIGS. 9, 10 and 11 are detailed views of the ratchet mechanism in accordance with the present invention.

DESCRIPTION OF THE PREFERRED EMBODIMENTS

Figure 1:
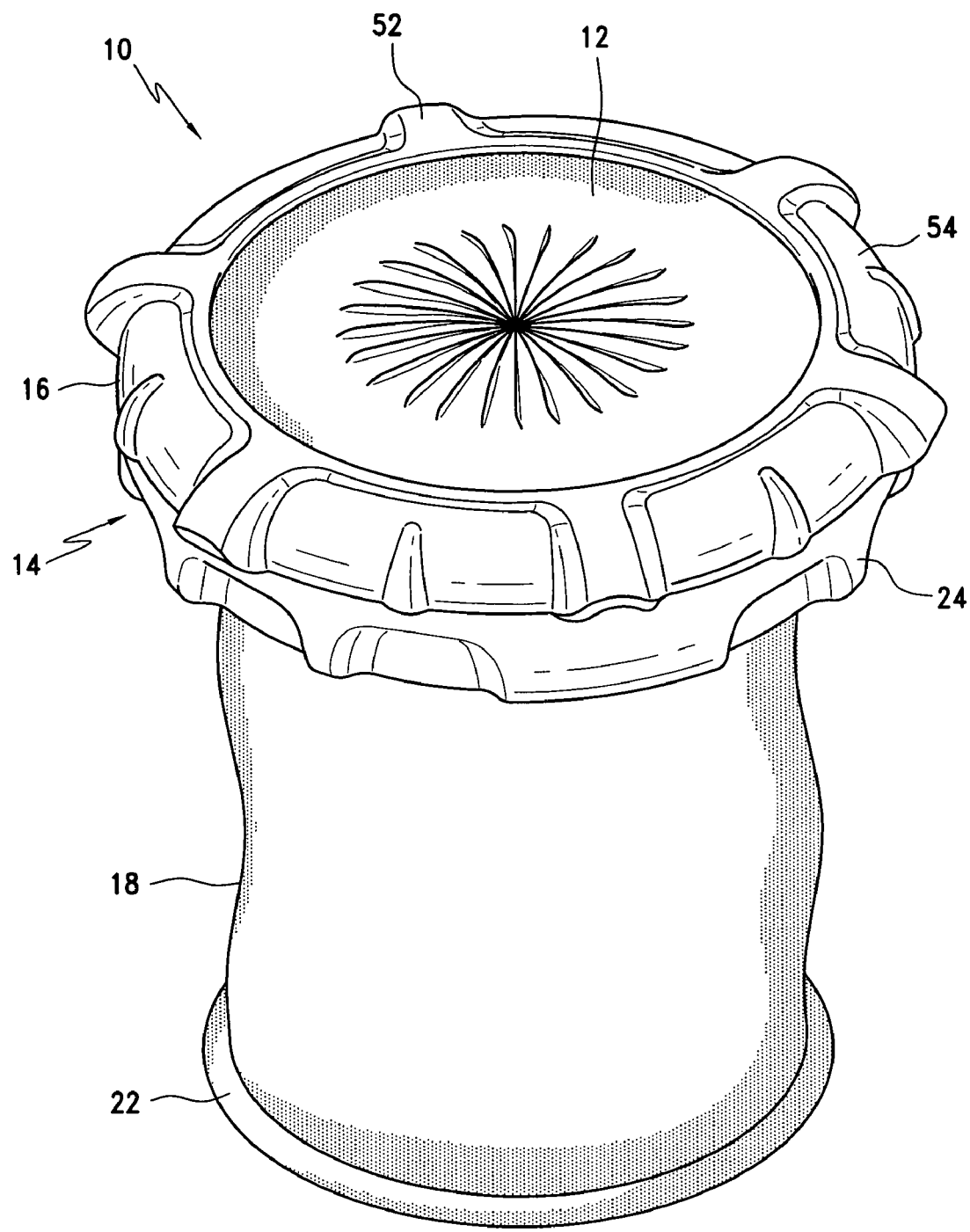
FIG. 1 is a perspective view of the present hand assisted laparoscopic seal assembly.
Figure 2:
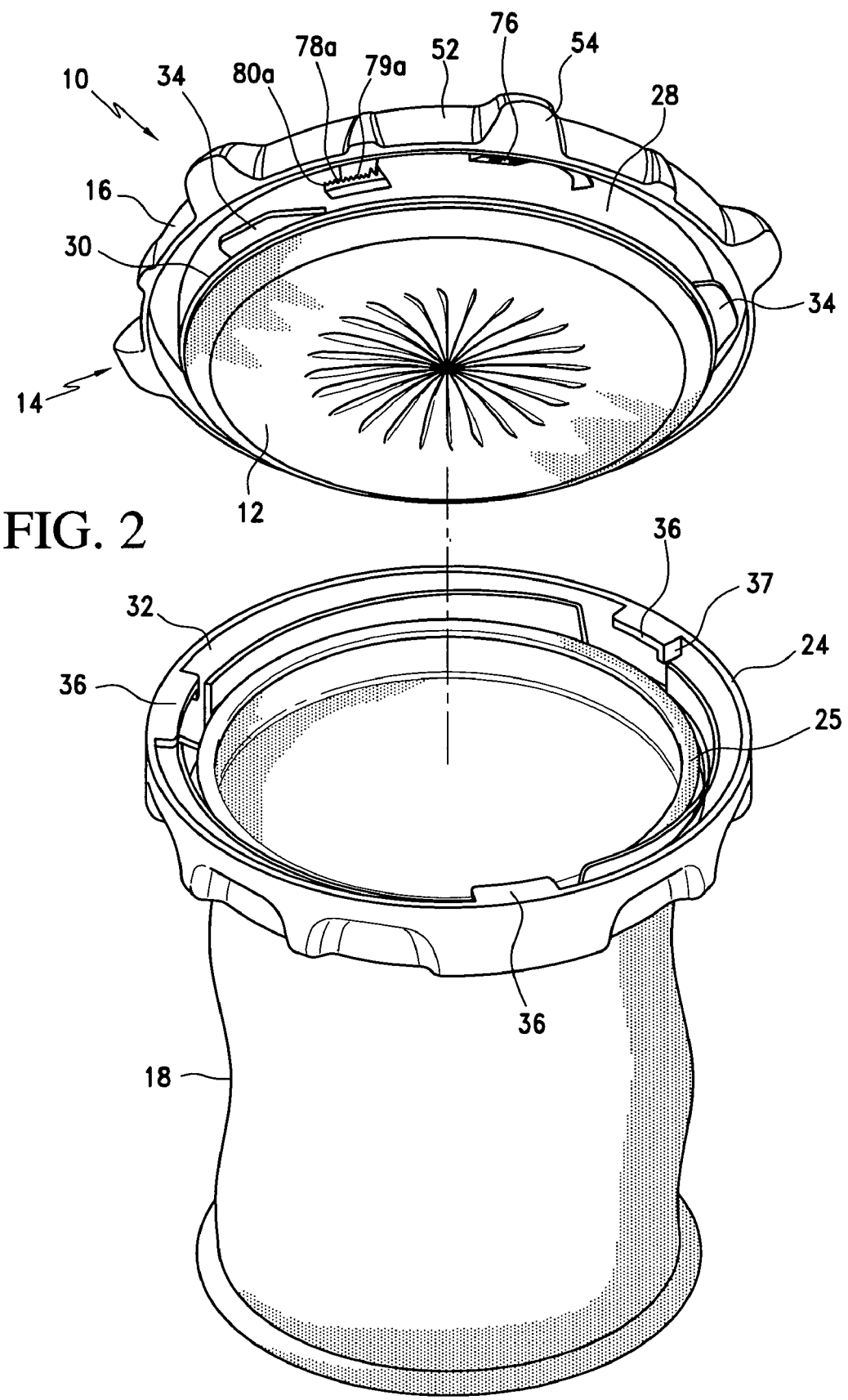
FIG. 2 is a perspective view of the hand assisted laparoscopic seal assembly with the attachment ring and retractor disengaged from the seal cap.
Figure 3:
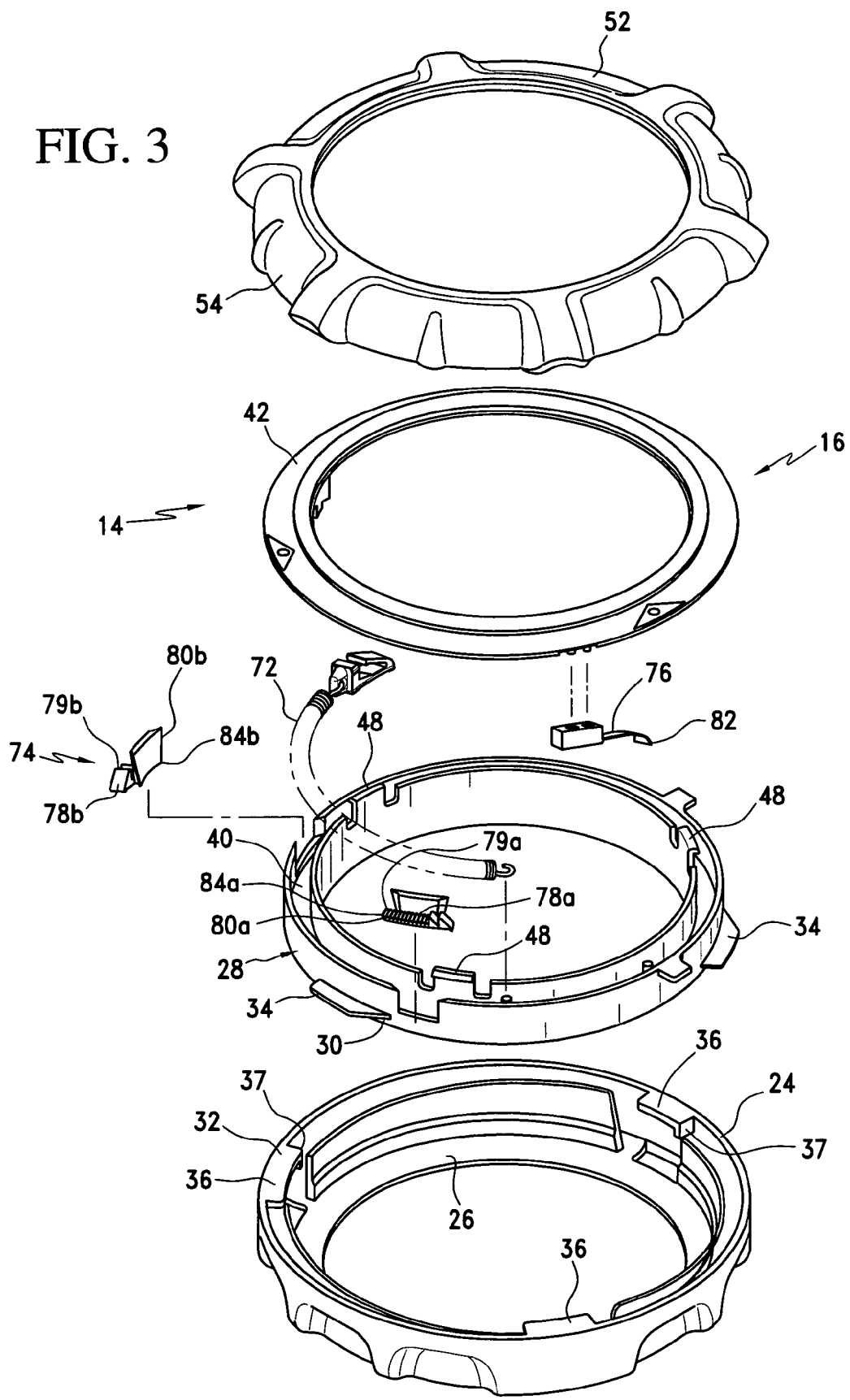
FIG. 3 is an exploded view of the seal cap of the present seal assembly.
Figure 4:
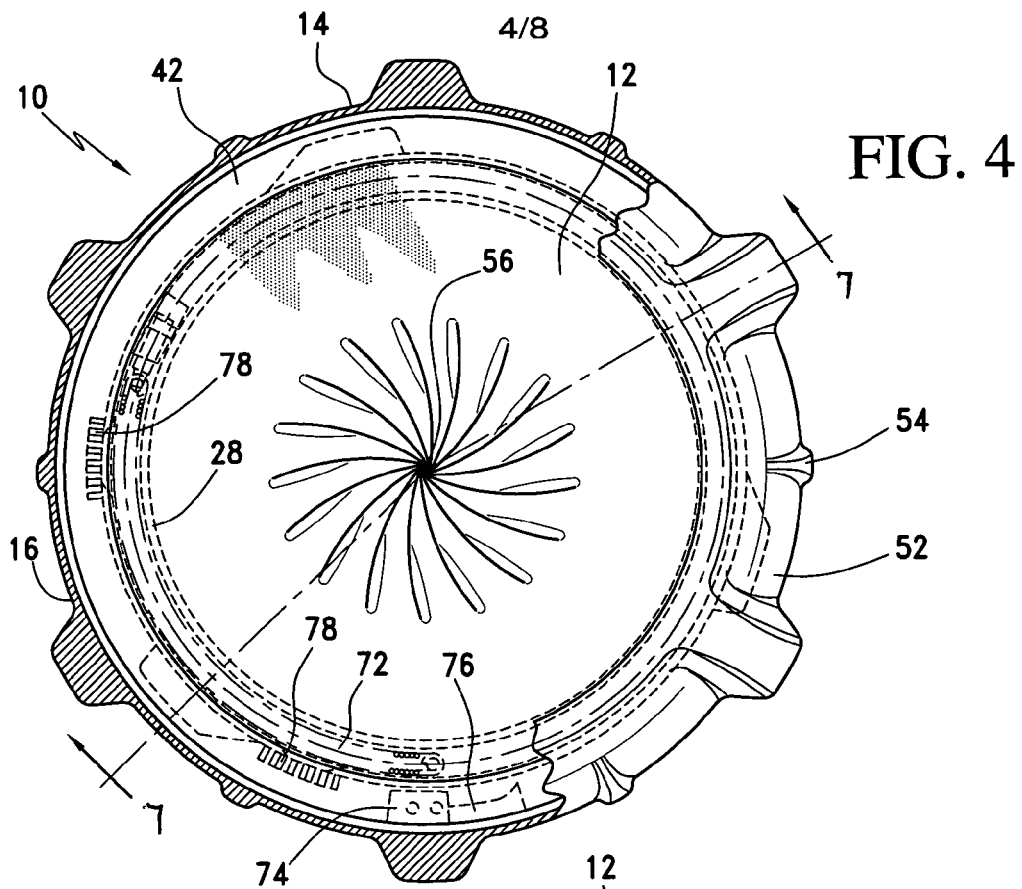

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

Referring to FIGS. 1 to 11, a seal assembly 10 for permitting hand assisted laparoscopic procedures is disclosed. The seal assembly 10 generally employs an iris seal cap 14 and retractor 18 to ensure abdominal pressure is not compromised during hand exchanges while hand assisted laparoscopic procedures are performed. As such, and in accordance with a preferred embodiment of the present invention, the seal assembly 10 includes an iris seal 12 housed within a seal cap 14. The iris seal 12 creates a gas tight barrier around the surgeon's wrist or surgical instrument when inserted through the seal assembly 10 and also creates a gas tight barrier between the interior abdominal space and the external environment when a hand is not inserted through the seal assembly 10.

Referring to the various figures, the seal cap 14 includes an iris seal 12 positioned within a housing 16. The housing 16 is made of soft textured material such as SANTOPRENE, or other like materials and supports the iris seal 12 in a concentric manner.

As with prior hand assisted laparoscopic seal assemblies, the housing 16 of the present seal assembly 10 is secured to the abdominal wall 20 of an individual patient by first creating an incision and positioning the retractor 18 and the seal cap 14 above the incision. Thereafter, the retractor 18, which will eventually be coupled to the seal cap 14, is inserted into the body cavity with the abdominal wall 20 therebetween. As such, the seal cap 14 is securely connected and supported on the outside of the abdominal wall 20 with the retractor 18 resiliently holding the abdominal wall 20 therebetween.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to attaching the present seal assembly 10. If the incision is too small, the incision is extended as required on each end to maintain the central position of the incision relative to the placement of the present seal assembly 10. Thereafter, the lower retractor ring 22 of the retractor 18 is inserted through the incision. Using one's fingers, the retractor 18 is seated evenly under the peritoneum and the area is swept to ensure the lower retractor ring 22 is not lying between tissue layers. Thereafter, the seal cap 14 is attached to the retractor 18 via an attachment ring 24, which may be rigid but is not limited to a specific material, and adjustments are made to ensure the seal assembly 10 is secured with the patient's abdomen maintaining pneumo. As those skilled in the art will certainly appreciate, the retractor may be a fixed length or adjustable length retractor. In either case the retractor 18 must fit the abdominal wall thickness to maintain stability and pneumo. As briefly discussed above, the present seal assembly 10 is provided with an attachment ring 24 that is detachable from the remaining portions of the housing 16 for permitting selective attachment of the retractor 18 to the present seal cap 14. It is further contemplated, the attachment ring 24 can facilitate other accessory cap attachments, such as instrument port cap. In particular, the upper end 25 of the retractor 18 is seated within a ledge 26 formed in the attachment ring 24 (best seen in FIG. 3). Thereafter, the attachment ring 24 is secured to the lower seal ring 28 such that the retractor 18 is captured between the attachment ring 24 and the lower seal ring 28.

Selective attachment and detachment of the attachment ring 24 from the lower seal ring 28 is achieved through the provision of interlocking engagement structures formed along the lower surface 30 of the lower seal ring 28 and the upper surface 32 of the attachment ring 24. In particular, the lower seal ring 28 is formed with a plurality of outwardly extending flanges 34 that are shaped and dimensioned for seating within inwardly facing recesses 36 formed along the attachment ring 24. As such, one need only twist the outwardly extending flanges 34 into the inwardly extending recesses 36 to securely couple the attachment ring 24 to the lower seal ring 28, and ultimately to the remainder of the housing 16 of the seal cap 14. Rotation is controlled by providing the recesses 36 with a wall 37 that stops rotation of the lower seal ring 28 relative to the attachment ring 24. The wall 37 is positioned on the side of the recess 36 that is in the same rotational direction as the direction to open the iris seal 12 (and in accordance with a preferred embodiment, clockwise). When it is desired to detach the attachment ring 24 from the lower seal ring 28, one need only turn the lower seal ring 28 in the opposite direction, that is, counter-clockwise in accordance with a preferred embodiment, with slight pressure to overcome the frictional interference between the outwardly extending flanges 34 of the lower seal ring 28 and the inwardly directed recesses 36 of the attachment ring 24 such that the flanges 34 and recesses 36 are unseated in a manner permitting separation of the attachment ring 24 and the lower seal ring 28. It will be understood by those skilled in the art that the disconnect torque must be greater than the rotational torque of the iris seal. Although the present invention discloses a bayonet type of connection, many other techniques can be applied without departing from the spirit of the present invention, for example, axial snaps or latches may be employed. Also, although the retractor is disclosed as being detachably secured to the seal cap 14, it may be fixedly secured thereto without departing from the spirit of the present invention.

In accordance with a preferred embodiment, the iris seal 12 is a rotatable seal which selectively opens to permit passage of a surgeon's hand therethrough and automatically closes in a manner creating a gas tight barrier between the interior abdominal space and the external environment whether or not a hand or instrument 38 is inserted through the seal assembly 10. In particular, the housing 16 in which the iris seal 12 is supported includes a lower seal ring 28 having a track 40 which supports an upper seal ring 42 for relative rotational motion in a manner discussed below in greater detail.

As will be discussed below in greater detail, the upper end 44 of the iris seal 12 is permanently connected to the upper seal ring 42. The lower end 46 of the iris seal 12 is permanently connected to the lower seal ring 28. The upper seal ring 42 and the lower seal ring 28 are connected together for relative rotational movement in a manner allowing for opening and closing of the iris seal 12. In accordance with a preferred embodiment, the upper seal ring 42 and the lower seal ring 28 are connected by at least three snap tabs 48 located on the lower seal ring 28 that are shaped and dimensioned to engage a recess 50 along the inner edge of the upper seal ring 42.

An ergonomic cover member 52 is secured to the upper seal ring 42. The ergonomic cover member 52 includes a contoured outer surface 54 providing for improved handling and twisting of the upper seal ring 42 for opening and closing the iris seal 12 in accordance with the present invention. In accordance with a preferred embodiment, the ergonomic cover member 52 is a separate component fixedly secured to the upper seal ring 42 such that rotational force applied to the ergonomic cover member 52 is transmitted on to the upper seal ring 42 for opening and closing of the iris seal 12. However, and as those skilled in the art will certainly appreciate, the ergonomic cover member 52 could be integrally formed with the upper seal ring 42, while still remaining within the spirit of the present invention.

Referring to FIGS. 4, 5, 6, 7 and 8, as discussed below in greater detail, the iris seal 12 is secured between the upper seal ring 42 and the lower seal ring 28. The upper seal ring 42 is supported within a track 40 of the lower seal ring 28 in a manner facilitating rotational movement between the upper seal ring 42 and the lower seal ring 28. In this way, the rotational movement of the upper seal ring 42 relative to the lower seal ring 28 is utilized to control the opening and closing of the iris seal 12 for one-hand insertion of a hand through the present seal assembly 10.

The iris seal 12 is mounted between the upper seal ring 42 and the lower seal ring 28 such that upon rotation of the upper seal ring 42 in a predetermined direction, the central access opening 56 of the iris seal 12 will open providing a surgeon with an access opening 56 for passage of his hand therethrough. Automatically the upper seal ring 42, and ultimately, the iris seal 12 will rotate in the reverse direction, the access opening 56 will close securely about the wrist of the surgeon or instrument. That is, the upper seal ring 42 and the iris seal 12 are moved between open orientations (see FIGS. 5, 6 and 8) in which an access opening 56 is created within the iris seal 12 and a closed orientation (see FIGS. 4 and 7) in which the iris seal 12 is either wrapped about the wrist of a user with his or her hand inserted therein or substantially fully closed when the iris seal 12 is not in use.

Opening and closing of the iris seal 12 is achieved by constructing the iris seal 12 in a folded configuration spanning the upper seal ring 42 and the lower seal ring 28 in a substantially taut configuration. As such, rotation of the upper seal ring 42 in a first direction will result in an increase of tension along the iris seal 12 in a manner drawing the fold outwardly opening the central access opening 56 in the iris seal 12.

Figure 7:
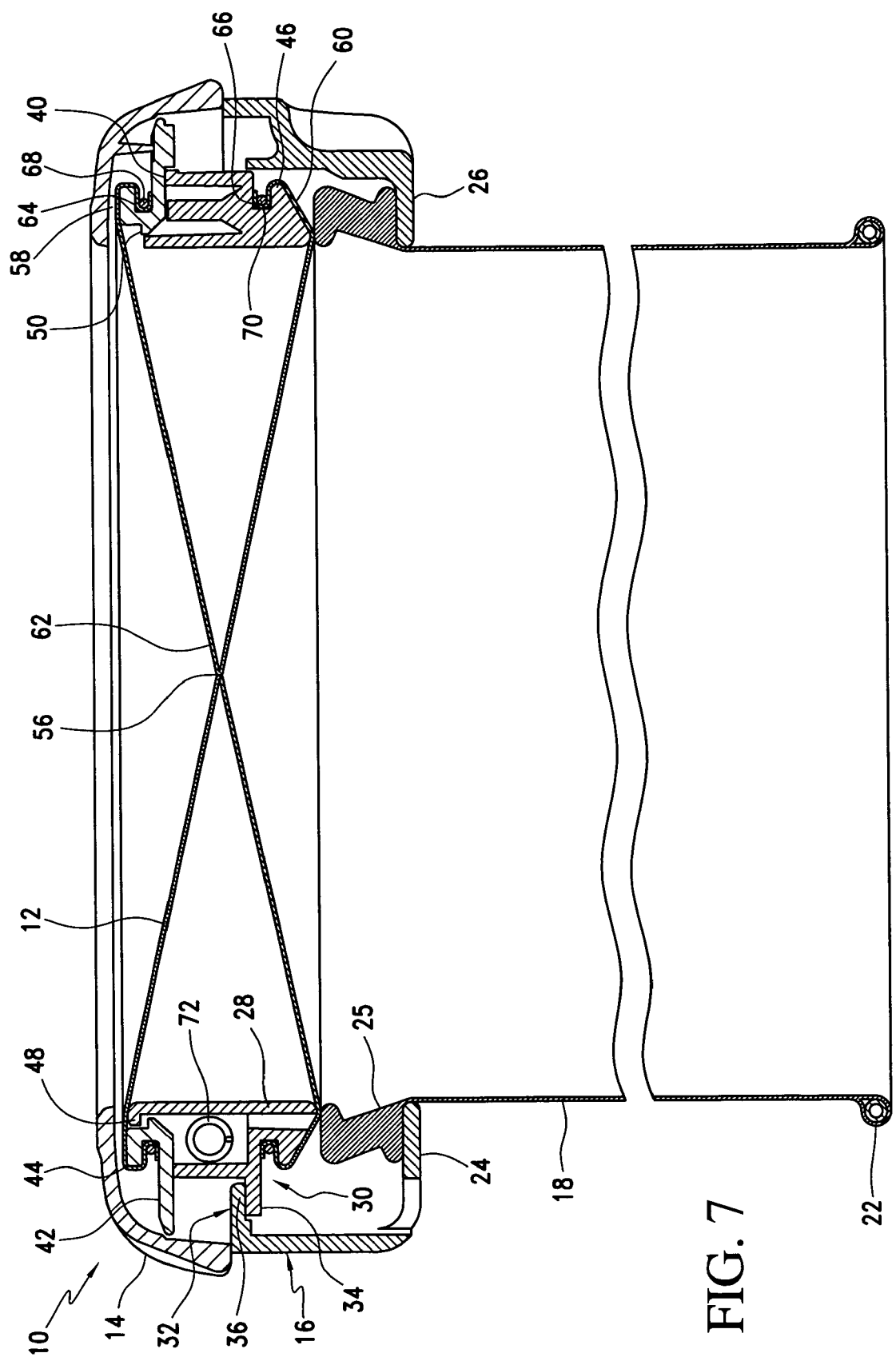
FIG. 7 is cross sectional view taken along the line 7-7 in FIG. 4.
Figure 8:
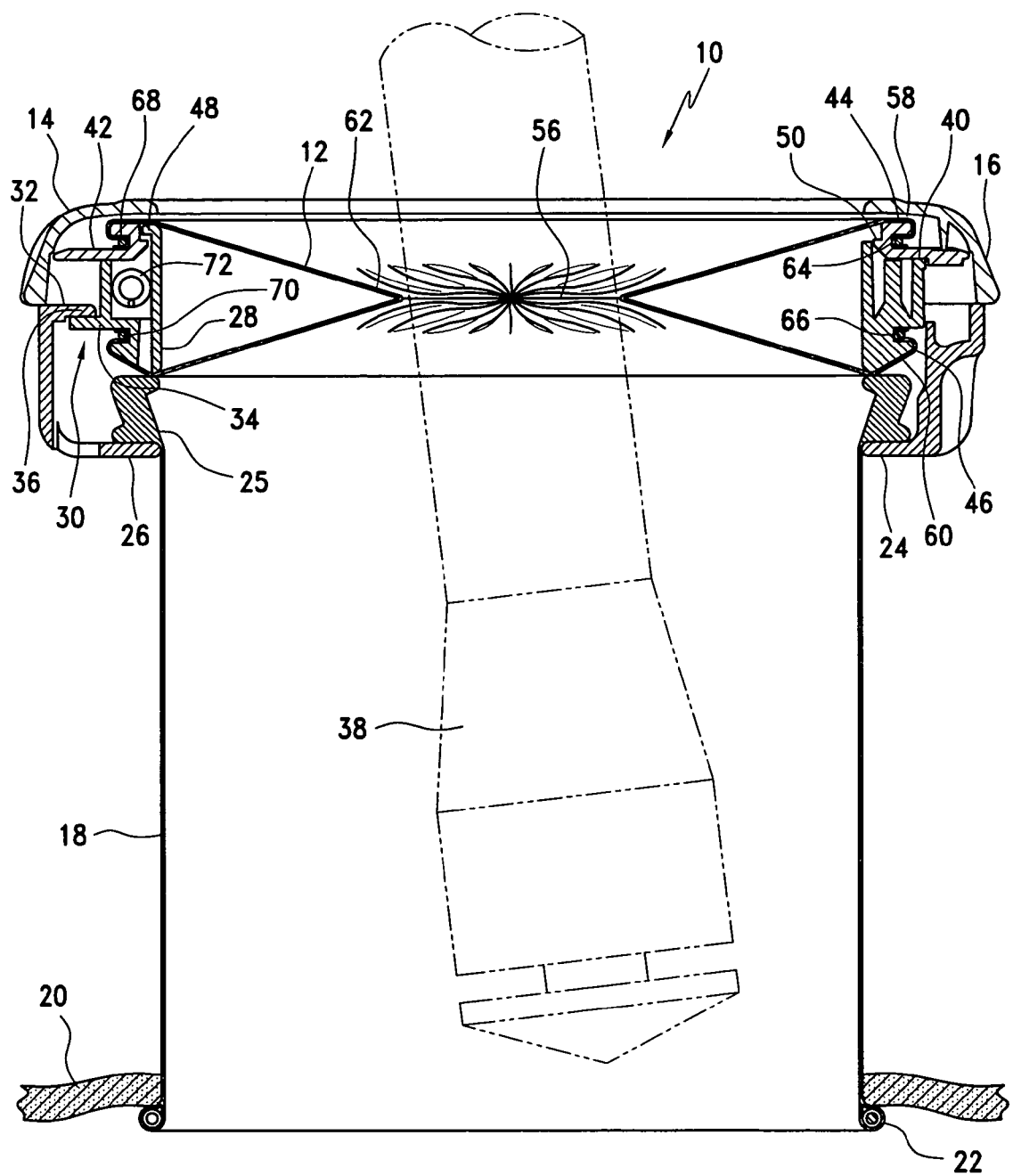
FIG. 8 is cross sectional view taken along the line 8-8 in FIG. 6 with an instrument shown in phantom.

In accordance with the preferred embodiment, the iris seal 12 is composed of a rubber like member. The rubber like member is constructed in the shape of a cylindrical section with the upper and lower sections 58, 60 thereof having a wider diameter than the central section 62 (thereby offering a generally I-shaped cross-section as shown in FIGS. 7 and 8 when assembled). As will be appreciated based upon the following disclosure, the construction of the rubber like member creates a substantially planar iris seal 12 which is closed or opened when the upper seal ring 42 and the lower seal ring 28 are relatively rotated in opposite directions.

In accordance with a preferred embodiment, the rubber like member is formed from a thin film having a thickness around 0.010" to 0.013" and made from a material having elasticity, such as, natural rubber, synthetic rubber, poly vinyl chloride, silicon and a variety of elastomers (for example, urethane, polyisoprene, silicone). As briefly mentioned above, the rubber like member is tapered cylindrical and includes a central access opening 56 having a predetermined cross sectional area at the central section 62 thereof. The rubber like member is shaped such that the diameter of the opening decreases in the direction from the upper and lower sections to the central section 62 of the rubber like member. Furthermore, the upper and lower ends 44, 46 of the iris seal 12, which are fitted into the grooves 64, 66 of the upper seal ring 42 and the lower seal ring 28 and held therein with o-rings 68, 70, allow for detachment from the upper seal ring 42 and the lower seal ring 28. In accordance with a preferred embodiment, the o-rings are integrated into the iris seal, minimizing components and material cost. Because of such detachable structure of the rubber like member, it can be easily replaced by a fresh member when the used rubber like member is broken or worn. This technique would be useful for reusable devices.

Figure 5:
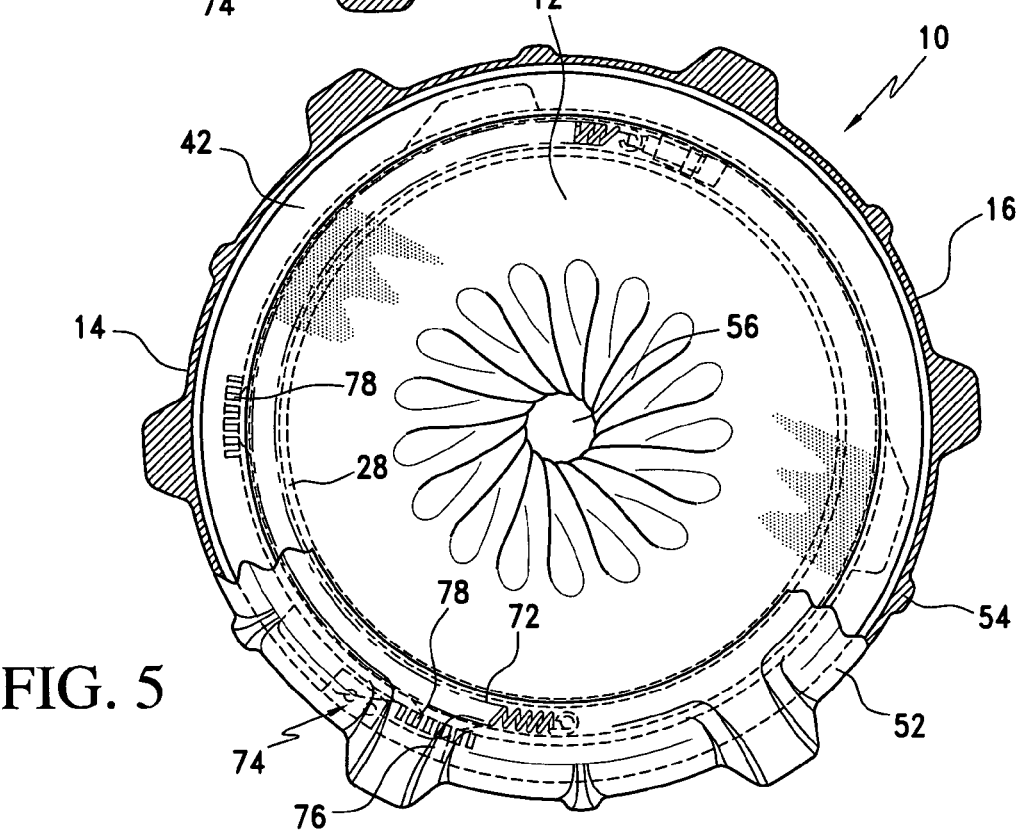

Referring to FIGS. 4, 5, 6, 7 and 8, a plan view and a sectional view are presented, showing the iris seal 12 in its respective closed and open states. FIGS. 6 and 8 show the iris seal 12 in a fully opened orientation for viewing within the cavity or insertion of an instrument or hand therethrough, while FIG. 5 shows a partially opened orientation sufficient for passing a hand therethrough when sealing thereabout is desired.

This open state is created when the upper seal ring 42 is rotated at a predetermined angle, for example, 15 degrees, from the closed state of the iris seal 12, and the access opening 56 is created.

Figure 12:
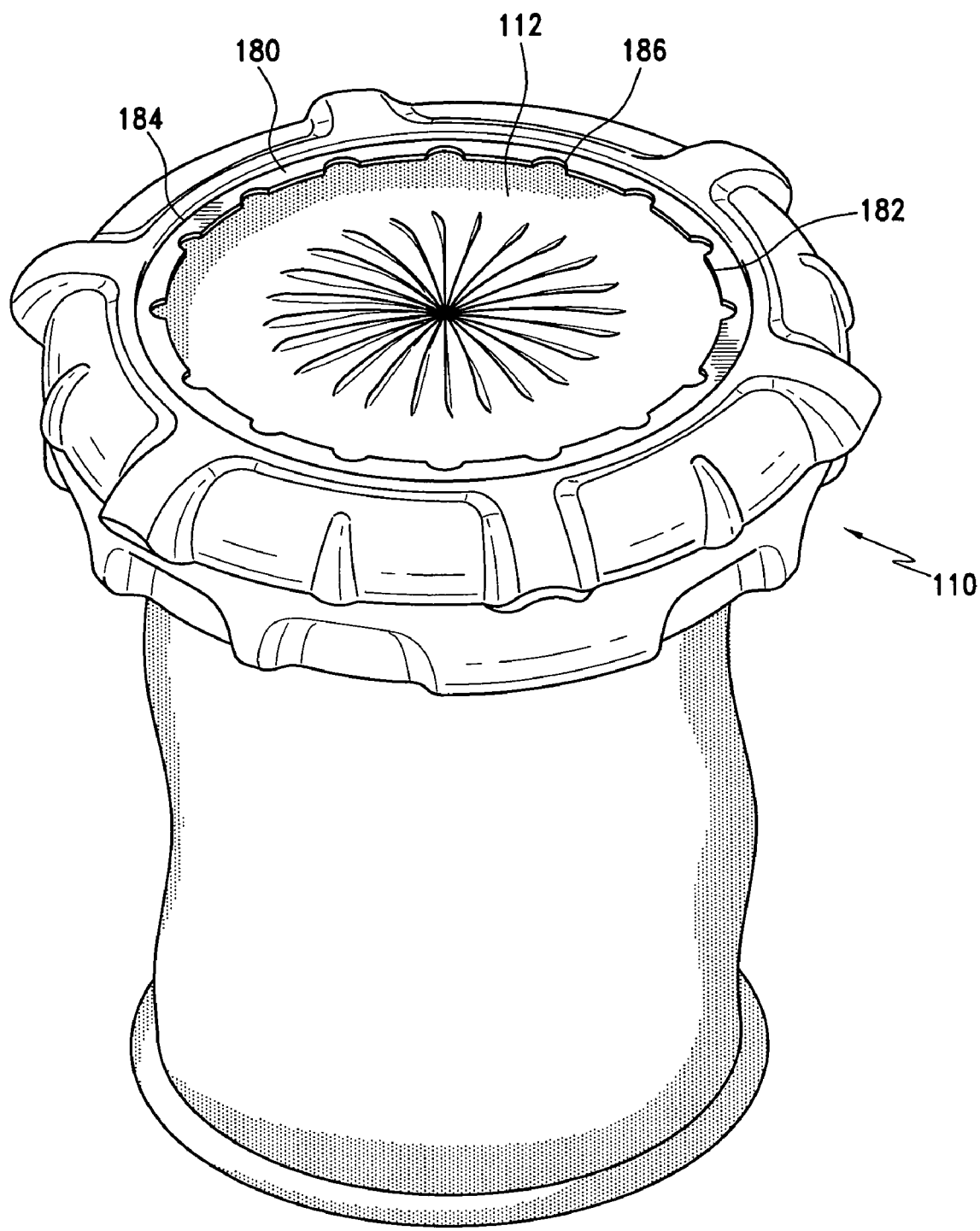
FIG. 12 is a perspective view of a hand assisted laparoscopic seal assembly in accordance with an alternate embodiment.

In accordance with an alternate embodiment, and with reference to FIG. 12, improved access to the movement of the upper seal ring, and ultimately, the iris seal 112, is achieved by the provision of a contoured ring 180 secured to the upper surface of the upper seal ring. The contoured ring 180 is substantially annular and includes and inner circumference 182 and an outer circumference 184. The outer circumference 184 is substantially smooth and conforms to the profile of the upper seal ring. However, the inner circumference 182 is formed with a series of recesses 186 shaped and dimensioned for receiving the fingers of a medical practitioner attempting to use the present seal assembly 110. In particular, the recesses 186 are shaped and dimensioned such that an individual wishing to use the present seal assembly 110 may seat his or her fingers therein and rotate the contoured ring, and the upper seal ring to which the contoured ring 180 is rigidly attached, and ultimately the iris seal 112 with only one hand. While the iris seal 112 is in its open orientation, the user may simply slip his or her hand through the iris seal 112 and proceed with the surgical procedure with minimal loss of insufflation. This feature allows the physician's other hand to be free and undisrupted, allowing the surgeon to maintain his procedural focus and position with the free hand during hand exchanges.

In accordance with a preferred embodiment, the upper seal ring 42 is biased relative to the lower seal ring 28 by a spring 72 to immediately return to the closed orientation upon rotation of the upper seal ring 42 relative to the lower seal ring 28 to its open orientation with subsequent release thereof. As such, the surgeon may rotate the upper seal ring 42 relative to the lower seal ring 28 through engagement of the contoured surface of the ergonomic cover member 52, the contoured ring 180 (in accordance with the embodiment shown with reference to FIG. 12) or the iris seal 12 to move the iris seal 12 from its closed orientation to an open orientation opening the access opening 56 for passage of his or her hand therethrough. Once his or her hand is passed therethrough, the upper seal ring 42, ergonomic cover member 52, contoured ring 180 and/or the iris seal 12 are released allowing the action of the spring 72 to move the upper seal ring 42 and the iris seal 12 back toward the closed orientation.

As some surgeons may want to maintain an open position using the auto-closing device, a ratchet mechanism 74 has been developed wherein the surgeon has control over the spring biased action moving the upper seal ring 42 relative to the lower seal ring 28 and iris seal 12 from its open orientation to its closed orientation. Although a ratchet system is disclosed in accordance with a preferred embodiment of the present invention, those skilled in the art will appreciate that a seal assembly without a ratchet assembly could also be practiced within the spirit of the present invention.

In accordance with a preferred embodiment, and with reference to FIGS. 3 to 11, the upper seal ring 42 is seated within the track 40 of the lower seal ring 28 with the spring 72 biasing the upper seal ring 42 relative to the lower seal ring 28 for movement relative thereto opening the access opening 56. However, a ratchet mechanism 74 is positioned between the upper seal ring 42 and the lower seal ring 28. The ratchet mechanism 74 includes a ratchet arm 76 secured to the upper seal ring 42 which is oriented to engage upwardly facing first and second ratchet surfaces 78*a*, 78*b* composed of a plurality of ratchet teeth 79*a*, 79*b* on the lower seal ring 28 which functions to hold the upper seal ring 42 relative to the lower seal ring 28 as it is moved to an open orientation. In practice, the ratchet arm 76 is shaped and dimensioned to engage the teeth 79*a*, 79*b* of the ratchet surfaces 78*a*, 78*b* when rotated in a first direction (for example, and in accordance with a preferred embodiment, clockwise rotation when viewed from above). However, once the upper seal ring 42 is rotated such that the ratchet arm 76 moves beyond the rear end 80*a*, 80*b* of the ratchet surfaces 78*a*, 78*b*, the ratchet arm 76 is free to move under the ratchet surfaces 78a, 78b as the upper surface ring 42 is rotated in a second direction opposite the first direction.

This is achieved by providing the ratchet arm 76 with a tapered distal end 82 which is biased by a similar tapered surface 84a, 84b on the respective rear end 80a, 80b of the ratchet surfaces 78a, 78b to ride under the ratchet surfaces 78a, 78b as the upper seal ring 42 is rotated relative to the lower seal ring 28 in a second direction. However, when the upper seal ring 42 is rotated in a first direction, the distal end 82 of the ratchet arm 76 is biased to ride over the upper surface of the ratchet surfaces 78a, 78b such that it engages the various teeth 79a, 79b to control movement of the upper seal ring 42 relative to the lower seal ring 28.

In accordance with a preferred embodiment of the present invention, first and second ratchet surfaces 78a, 78b are provided. The first ratchet surface 78a engages the ratchet arm 76 when the upper and lower seal rings 42, 28 are oriented to provide a relatively small opening in the iris seal 12 through which a medical practitioner may pass his or her hand to gain access to a body cavity. The configuration is especially suited to single hand interactions where a user may rotate the upper seal ring 42 relative to the lower seal ring 28 with the same hand which is to be passed through the present seal assembly 10. In particular, and as a result of the ratchet mechanism 74, a user may, for example, use his or her left hand to rotate the upper seal ring 42 relative to the lower seal ring 28 in a manner slightly or partially opening the iris seal 12 as shown in FIG. 5. When in this position, the audible click sound and slight resistance produced as the ratchet arm 76 moves over the first ratchet surface 78a will provide the user with an indication a stopping position has been reach. At this point, the user may release the upper seal ring 42 without fear that the iris seal 12 will snap back to its closed orientation. Rather, the ratchet mechanism 74 holds the upper and lower seal rings 42, 28 relative to each other, allowing the user to slip his or her hand through the opening in the iris seal 12. As the user pushes his or her hand through the iris seal 12, the outward force causes a slight rotation of the upper seal ring 42 relative to the lower seal ring 28 in a manner disengaging the ratchet arm 76 from the first ratchet surface 78a, and allowing the upper seal ring 42 to rotate relative to the lower seal ring 28 under the bias of the spring 72 to move the iris seal 12 back to its closed orientation, securely wrapping it about the user's wrist/forearm. As such, when the user must pull his or her arm from the seal assembly 10, the iris seal 12 will automatically close sealing the body cavity from the external environment.

The second ratchet surface 78b allows the seal assembly 10 to be locked in a larger open configuration allowing for more complete access to the body cavity. As those skilled in the art will certainly appreciate, it is at times desirable to provide a large access opening to the body cavity. As such, the present seal assembly 10 is provided with a second ratchet surface 78b providing for locking of the upper seal ring 42 and the lower seal ring 28 relative to each other when the iris seal 12 is more fully opened as shown in FIG. 6. As with the first ratchet surface 78a, the second ratchet surface 78b engages the ratchet arm 76 when the upper and lower seal rings 42, 28 are oriented in a particular orientation providing, in this case, a relatively large opening in the iris seal 12. A user rotates the upper seal ring 42 relative to the lower seal ring 28 to create an opening in the iris seal 12 beyond the small opening as shown in FIG. 5. Once the first ratchet surface 78a is passed (as indicated by the first series of audible clicks), the audible clicking sound produced as the ratchet arm 76 moves over the second ratchet surface 78b will provide the user with an indication a stopping position has been reached. At this point, the user may release the upper seal ring 42 without fear that the iris seal 12 will close, and proceed to utilize the large opening for access to the body cavity in a desired manner. When the user no longer requires this access, he or she may simply rotate the upper seal ring 42 relative to the lower seal ring 28 in a first direction slightly opening the iris seal 12, at which point the ratchet arm 76 will disengage from the second ratchet surface 78b and allow the upper seal ring 42 to rotate relative to the lower seal ring 28 under the bias of the spring 72 to move the iris seal 12 back to its closed orientation.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A seal assembly for permitting hand assisted laparoscopic procedures, comprising:
    a seal cap including a seal positioned within a housing, the housing including a lower seal ring having a track which supports an upper seal ring for relative rotational motion, wherein the seal is supported between the upper seal ring and the lower seal ring for rotation between an open orientation and a closed orientation;
    a spring biasing the upper seal ring relative to the lower seal ring; and
    a ratchet mechanism controlling motion of the upper seal ring relative to the lower seal ring the ratchet mechanism includes a ratchet arm oriented to engage a ratchet surface composed of a plurality of ratchet teeth, the ratchet arm being shaped and dimensioned to engage the ratchet teeth of the ratchet surface when rotated in a first direction until the ratchet arm moves beyond a rear end of the ratchet surface, where the ratchet arm is free to move past the ratchet surfaces and rotate in a second direction opposite the first direction.

2. The seal assembly according to claim 1, further including a retractor extending from the seal cap.

3. The seal assembly according to claim 2, wherein the housing further includes an attachment ring detachably secured to the lower seal ring for permitting selective attachment of the retractor by positioning it between the attachment ring and the lower seal ring.

4. The seal assembly according to claim 3, wherein the lower seal ring includes at least one outwardly extending flange shaped and dimensioned for seating within at least one inwardly facing recess formed along the attachment ring.

5. The seal assembly according to claim 1, where an upper end of the seal is connected to the upper seal ring and a lower end of the iris seal is connected to the lower seal ring.

6. The seal assembly according to claim 1, further including an ergonomic cover member secured to the upper seal ring, wherein the ergonomic cover member includes a contoured outer surface providing for improved handling and twisting of the upper seal ring for opening and closing the seal.

7. The seal assembly according to claim 1, wherein the seal is an iris seal.

8. The seal assembly according to claim 7, wherein the iris seal is constructed in a folded configuration spanning the upper seal ring and the lower seal ring.

9. The seal assembly according to claim 7, wherein the iris seal is composed of a rubber like member.

10. The seal assembly according to claim 1, further including a contoured ring secured to the upper seal ring, the contoured ring including an inner circumference formed with a series of recesses shaped and dimensioned for receiving fingers of a user.

11. The seal assembly according to claim 1, wherein the ratchet arm is shaped and dimensioned to engage the ratchet surface when the upper seal ring is rotated relative to the lower seal ring in the first direction and rides under the ratchet surface when the upper seal ring is rotated relative to the lower seal ring in the second direction.

12. The seal assembly according to claim 11, wherein the ratchet arm includes a tapered distal end shaped and dimensioned to ride under the ratchet surface as the upper seal ring is rotated relative to the lower seal ring in the second direction.

13. The seal assembly according to claim 1, wherein the ratchet arm is secured to the upper seal ring and the ratchet surface is on the lower seal ring.

14. The seal assembly according to claim 13, further including first and second ratchet surfaces on the lower seal ring.

15. The seal assembly according to claim 1, further including first and second ratchet surfaces.

* * * * *